United States Patent [19]

Rajlevsky

[11] Patent Number: 4,955,873

[45] Date of Patent: Sep. 11, 1990

[54] STABILIZING SUPPORT STAND

[75] Inventor: Jack Rajlevsky, Rego Park, N.Y.

[73] Assignee: Pfizer Hospital Products Group, Inc., New York, N.Y.

[21] Appl. No.: 190,795

[22] Filed: May 6, 1988

[51] Int. Cl.[5] .............................................. A61M 1/00
[52] U.S. Cl. ........................... 604/322; 128/DIG. 24; 248/97; 248/188.6
[58] Field of Search ....................... 604/317, 322–326, 604/319; 128/760, 767, DIG. 24; 248/95, 97, 188.6, 188.7, 359 E, 528

[56] References Cited

U.S. PATENT DOCUMENTS

| | | | |
|---|---|---|---|
| 1,971,642 | 8/1934 | Champlin | 248/97 |
| 2,572,205 | 10/1951 | Shanks | 248/188.6 |
| 3,222,019 | 12/1965 | Weisberg | 248/97 |
| 3,559,942 | 2/1971 | Lucasey | 248/188.6 |
| 3,724,798 | 4/1973 | Lucasey | 248/418 |
| 4,288,052 | 9/1981 | Scott | 248/188.6 |
| 4,363,460 | 12/1982 | Carroll | 248/415 |
| 4,439,190 | 3/1984 | Protzmann et al. | 604/319 |
| 4,449,969 | 5/1984 | Schweizer | 604/322 |
| 4,744,536 | 5/1988 | Bancalari | 248/188.6 |
| 4,763,866 | 8/1988 | Sinchok | 248/188.7 |
| 4,784,642 | 11/1988 | Everett, Jr. et al. | 604/118 |

Primary Examiner—Stephen C. Pellegrino
Assistant Examiner—Ralph Lewis
Attorney, Agent, or Firm—Peter C. Richardson; Lawrence C. Akers; John L. LaPierre

[57] ABSTRACT

A support stand, particularly suitable for use in securing an article against overturn, being coupled to the article in a locked article stabilizing position. Preferably, the stand is rotatively coupled to the article for selective location of the stand in either an inoperative position or in a locked operative article stabilizing position.

14 Claims, 3 Drawing Sheets

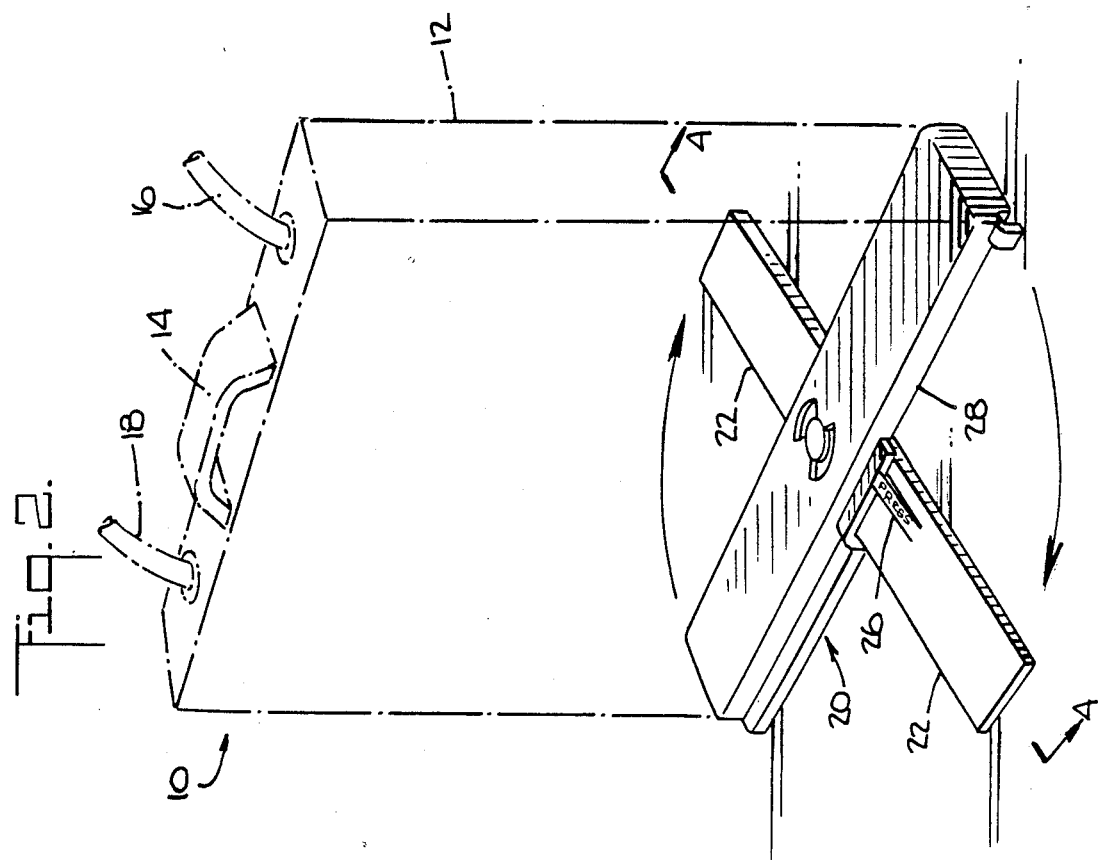
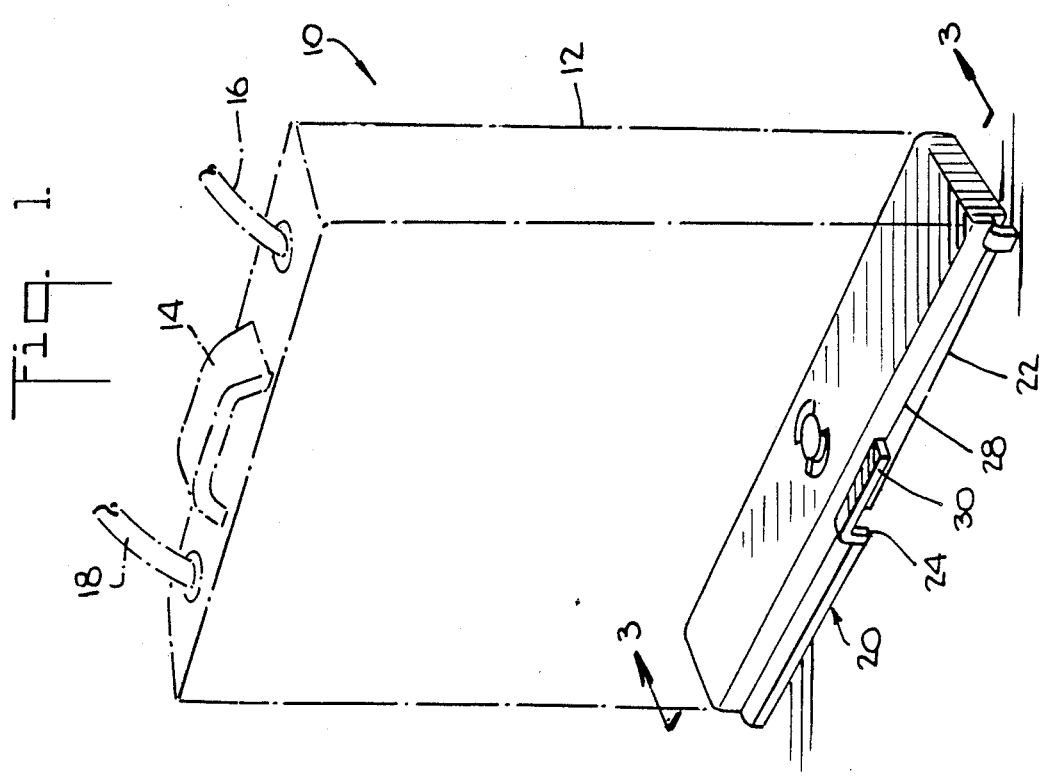

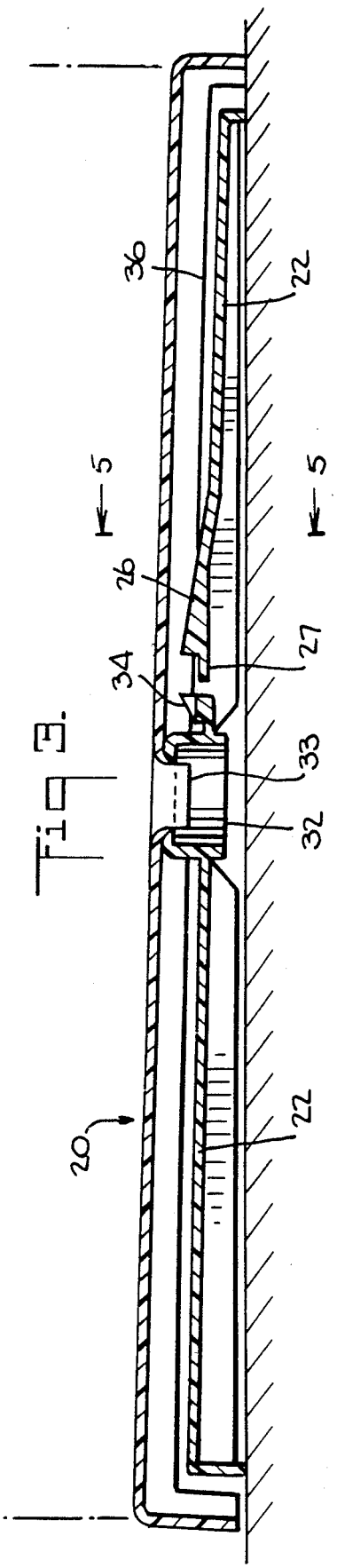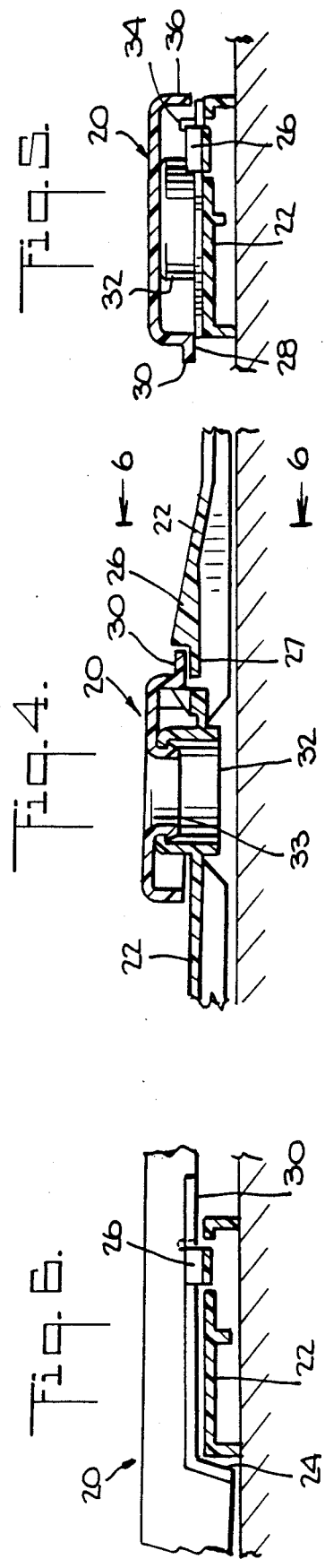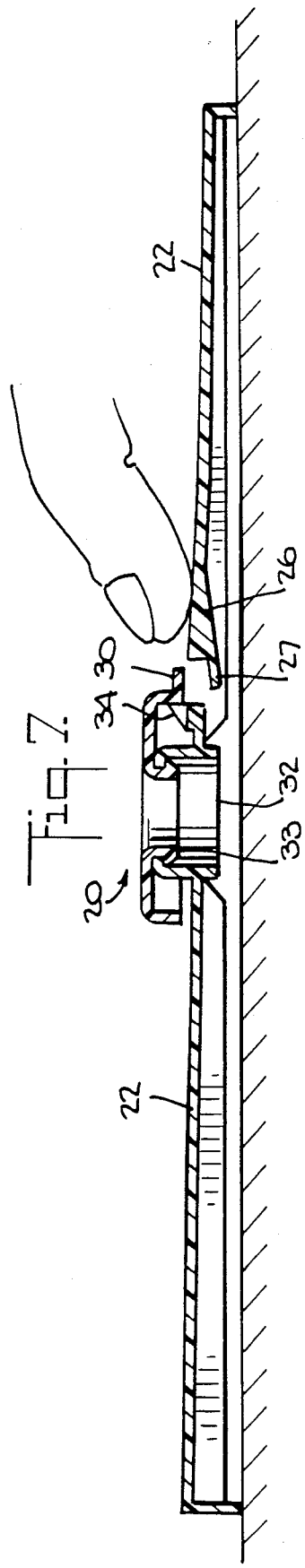

STABILIZING SUPPORT STAND

BACKGROUND OF THE INVENTION

The present invention relates generally to article support devices and, more particularly, it relates to stands suitable in use to effect the securing of a body against upset or overturn. The stand finds a preferred use in stabilizing a drainage receptacle, used chiefly during surgical procedures and for post operative patient care for receiving and collecting fluids drained from the patient, by securing the receptacle in an upright position. Positioning and stabilizing the drainage device in an upright orientation enhances the receptacle to patient connection and helps maintain the integrity of the fluids collected.

There have been a number of devices introduced to the marketplace for use as a base or stand in an effort to keep a drainage collection unit upright. However, no known device locks a support stand in a fully deployed position. Accordingly, many known drainage devices are susceptible to being easily upset. For example, an existing drainage collection apparatus support stand might be kicked and, if the stand is not locked against movement, the stand might fold up or return to its inoperative non-support position and cause unit overturn. A fluid collection device which is upset can create a critical situation by dislodging one or more tubes connected to a patient, such a result could cause fluid buildup in the patient or, in the case of a chest cavity being drained, could cause lung collapse. An additional unsatisfactory condition resulting from device overturn might be the mixing of collected fluids which are segregated in the device for volume versus time assessment or like purposes.

The primary objective of the present invention is to further advance the art field by providing a device which guards against body overturn and which, as can be seen from the foregoing, is particularly important when the stand is associated with a drainage receptacle. The conditions encountered when the present support stand or pedestal is used with a drainage receptacle and locked in a receptacle stabilizing position lessens or eliminates the disadvantages aforementioned with respect to conventional known support apparatus. Accordingly, I have invented an improved receptacle stabilizing device which provides additional improvement to presently available support devices.

SUMMARY OF THE INVENTION

The invention pertains to a stand for stabilizing or securing a body or article against overturn. The body may especially be a drainage device designed and configured to receive and collect fluids form a patient. The invention comprises at least one stand coupled to the body and adapted for deployment in a position for stabilizing the body against upset and includes means for locking the stand in the body stabilizing position. In a preferred form, the stand comprises at least one member rotatively coupled to the body and adapted for movements between first and second positions, with the member at the second position stabilizing the body against upset, and means for locking the member in the second body stabilizing position. The stand locking feature comprises one or more resilient fingers included on the member with the finger having a ramp or sloping face which cooperates with the body during member rotation. During rotation, the finger deflects and, after the member reaches the second body stabilizing position, the finger returns to its predeflection or rest position to effect a lock for restraining the member against rotation. The first and second member positions may be spaced from one another any number of degrees of rotation with a preferred orientation being substantially at right angles. Also contemplated within the scope of the invention is a means for preventing member rotation beyond the second or body stabilizing position. The locking finger, after deployment at the body stabilizing position, may be released to free the member and allow for member return to the first position.

The various features of novelty which characterize the invention are pointed out with particularity in the claims annexed to and forming a part of this disclosure. For a better understanding of the invention, its operating advantages and specific results obtained by its use, reference should be made to the corresponding drawings and descriptive matter in which there is illustrated and described a typical embodiment of the invention.

BRIEF DESCRIPTION OF THE DRAWINGS

FIG. 1 is a perspective view of a body stabilizing support stand, in accordance with the principles of the present invention, showing the support stand in a first inoperative position and further showing a drainage receptacle, in phantom, located above the stand.

FIG. 2 is a view of the stand and drainage receptacle substantially like that depicted in FIG. 1 but with the stabilizing support stand shown rotated to a locked second operative body stabilizing position.

FIG. 3 is an enlarged longitudinal cross-sectional view of the stand and the base of the drainage receptacle taken along line 3—3 of FIG. 1.

FIG. 4 is an enlarged partial longitudinal cross-sectional view taken along line 4—4 of FIG. 2 and showing a portion of the stand and a portion of the base of the drainage receptacle.

FIG. 5 is a transverse cross-sectional view of the stand and base taken along line 5—5 of FIG. 3.

FIG. 6 is a partial transverse cross-sectional view of the stand and base taken along line 6—6 of FIG. 4.

FIG. 7 is a view like that illustrated in FIG. 4 but showing the view in full section and illustrating release of the lock which secured the support stand in the second body stabilizing position.

DETAILED DESCRIPTION OF THE PREFERRED EMBODIMENT

Figure 8:
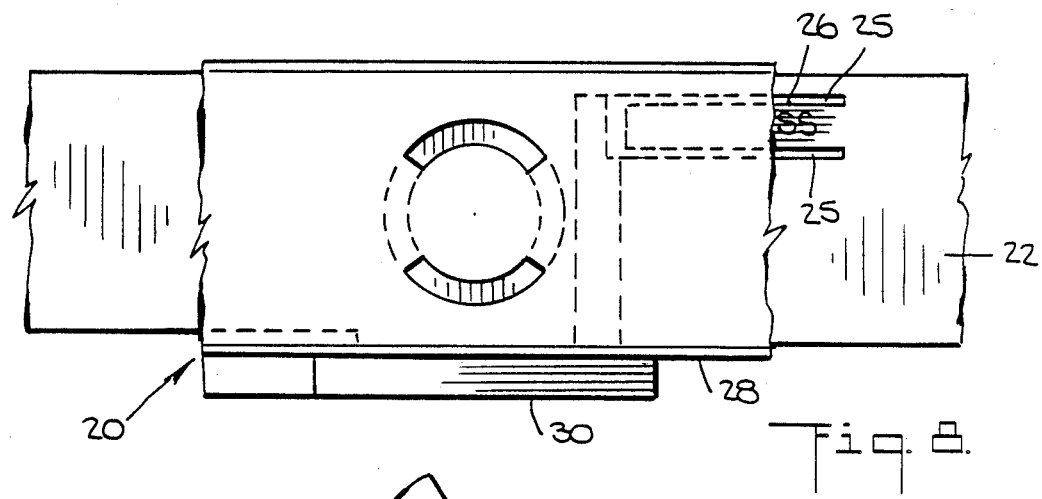
FIGS. 8-10 are enlarged partial top plan views of the body support stand and the base of the drainage receptacle illustrating, sequentially, rotation of the stand from a first inoperative position to a locked second operative body stabilizing position.

The description herein presented refers to the accompanying drawings in which like reference numerals refer to like parts throughout the several views. First turning to FIG. 1, there is illustrated a perspective representation of drainage receptacle 10, with housing portion 12 forming a collection chamber for collecting fluids drained from a patient, handle 14, patient connection tube 16 for draining patient fluids and suction source connection tube 18, all shown in phantom, having base portion 20 and pedestal or stabilizing member 22. In this view, stabilizing member 22 is in a first inoperative or stored position, that is, the member is not yet deployed into its body stabilizing position.

Turning now to FIG. 2, there is shown a view like that depicted in FIG. 1 but now showing stabilizing member 22 in a fully deployed, second body stabilizing position. Member 22 has been manually rotated from first to second position in the direction shown by the arrows and rotation beyond the position shown is prevented as member 22 contacts wall surface 24 (FIG. 1) of base 20. Stabilizing member 22 includes resilient finger 26 or like projection disposed therein, which finger acts to releasably lock member 22 in the position shown. During rotation of member 22 from first to second positions, finger 26, having a sloping or ramp face, coacts with lower surface of wall 28 of base portion 20 and is deflected downwardly. Upon full rotation of member 22 to the stabilizing position, finger 26 returns to its predeflection state, rising above the lower segment of wall 30 and essentially coming into abutting relationship with wall 30, locking member 22 in place.

Next turning to FIGS. 3–6, there are shown several sectional views which depict the construction and relationship between member 22 and base 20. Particularly from FIGS. 3 and 4, it can be seen that central portion 32 of member 22 is coupled to base 20 for rotation thereabout. Here, portion 32 is shown coupled to projection 33 extending from base 20. Also shown in FIG. 3 are upwardly projection piece 34, upwardly sloping or ramp face of finger 26 and back wall 36 of base 20. As seen, piece 34 and top of finger 26 extend above bottom of wall 36. While finger 26 is resilient and may be deflected downwardly (FIG. 7), piece 34 and wall 36 are rigid. Thus, contact of either piece 34 or non-deflected finger 26 would engage wall 36 and prevent rotation of member 22 in a direction other than that shown in FIG. 2. Also shown in these views, particularly in FIGS. 3 and 4, is that finger 26 may include a shelf 27 at the end thereof for engagement with the underside of wall 30 to limit the upward movement of finger 26 and ensure that finger 26 functions as intended, namely, locking member 22 against rotation.

FIG. 7 shows that, simply by depressing finger 26, member 22, through reverse rotation, is free to return to the position illustrated in FIG. 1. The interference between wall 30 and finger 26 has been eliminated and, with finger 26 deflected sufficiently, member 22 and finger 26 clear the lowermost portion of wall Z8 allowing for manual rotation of member 22 to the first position of FIG. 1.

Figure 9:
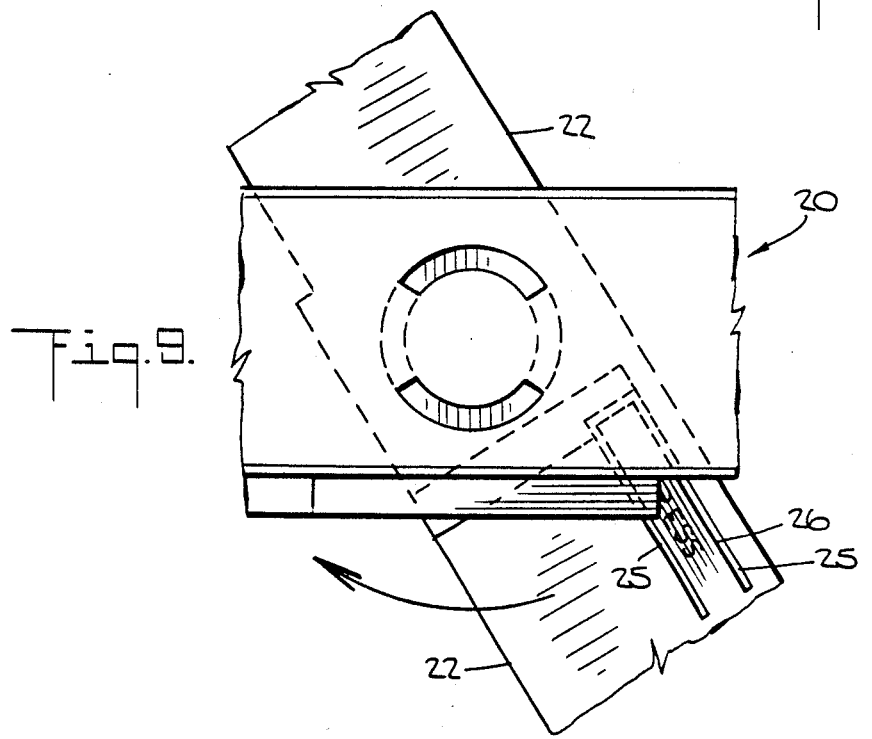
Figure 10:
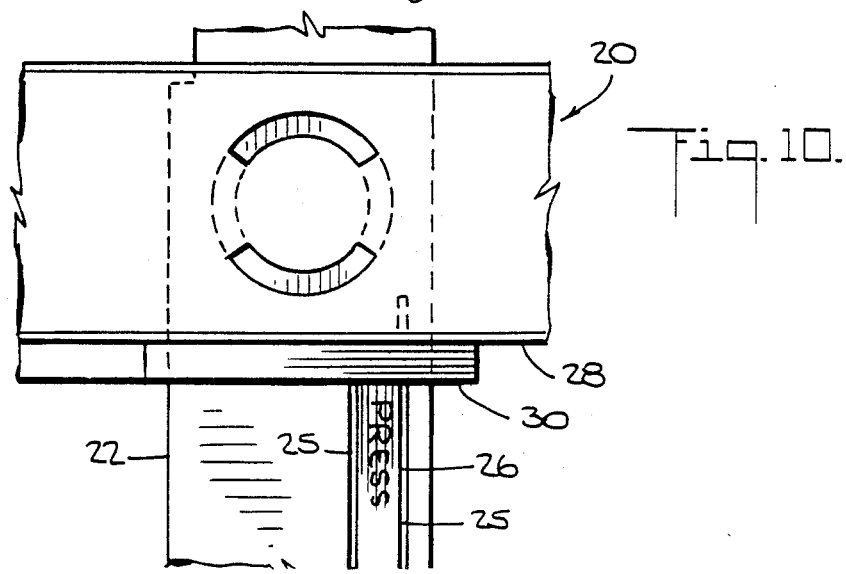

Lastly, turning to FIGS. 8–10, there are shown, sequentially, rotation of member 22 from a first position (FIG. 8), corresponding to the member position indicated in FIG. 1, to a second locked position (FIG. 10), corresponding to the member positioning of FIG. 2. The rotational direction followed by member 22 is indicated by the arrow shown in FIG. 9. As can be seen in these views, finger 26 is an integral part of member 22. Slots 25 indicate where material has been removed from member 22 during manufacture of member 22 and formation of finger 26. Material removal and ramping of finger 26 allows for finger deflection and, with appropriate selection of finger composition, the finger is made resilient.

While in accordance with provisions of the statutes there is described herein a specific embodiment of the invention, those skilled in the art will understand that changes may be made in the form of the invention covered by the claims appended hereto without departing from the scope and spirit thereof, and that certain features of the invention may sometimes be used to an advantage without corresponding use of the other features.

I claim:

1. A stand particularly suitable for use in stabilizing a drainage receptacle designed and configured to receive and collect fluids from a patient comprising a pedestal with means for nondetachable coupling to a box of said receptacle and adapted for deployment in a position for stabilizing said receptacle against upset, and means of unitary structure formed in a surface of said pedestal for positively mechanically locking said pedestal at said receptacle stabilizing position.

2. A stand particularly suitable for use in stabilizing a drainage receptacle designed and configured to receive and collect fluids from a patient comprising a pedestal with means for rotatively coupling to said receptacle and adapted for movement between first and second positions, with said pedestal at said second position stabilizing said receptacle against upset, and means of unitary structure formed in a surface of said pedestal for positively mechanically locking said pedestal at said second position rendering said pedestal non-rotative between said positions.

3. The stand according to claim 2 wherein said locking means comprises at least one resilient finger disposed in said pedestal.

4. The stand according to claim 3 wherein said finger includes a ramp face adapted for cooperative coaction with said receptacle during pedestal rotation, with said finger first being deflected and subsequently returning to the predeflection state after said pedestal reaches said second position.

5. The stand according to claim 2 wherein said pedestal in said second position assumes an orientation substantially perpendicular to that of said pedestal in said first position.

6. The stand according to claim 2 wherein said locking means is a releasable locking means adapted for release to free said pedestal for rotation to said first position.

7. The stand according to claim 2 further including means for preventing rotation of said pedestal beyond said receptacle stabilizing position.

8. A drainage receptacle and stand in combination comprising a housing forming a collection chamber for collecting fluids drained from a patient, an inlet in said housing adapted to be connected to said patient for draining said fluids from said patient, a pedestal nondetachably coupled to a base of said receptacle and adapted for deployment in a position for stabilizing said receptacle against upset, and means of unitary structure formed in a surface of said pedestal for positively mechanically locking said pedestal at said receptacle stabilizing position.

9. A drainage receptacle and stand in combination comprising a housing forming a collection chamber for collecting fluids drained from a patient, an inlet in said housing adapted to be connected to said patient for draining said fluids from said patient, a pedestal rotatively coupled to said receptacle and adapted for movement between first and second positions, with said pedestal at said second position stabilizing said receptacle against upset, and means of unitary structure formed in a surface of said pedestal for positively mechanically locking said pedestal at said second position rendering said pedestal non-rotative between said positions.

10. The combination according to claim 9 wherein said locking means comprises at least one resilient finger disposed in said pedestal.

11. The combination according to claim 10 wherein said finger includes a ramp face adapted for cooperative coaction with said receptacle during pedestal rotation, with said finger first being deflected and subsequently returning to the predeflection state after said pedestal reaches said second position.

12. The combination according to claim 9 wherein said pedestal in said second position assumes an orientation substantially perpendicular to that of said pedestal in said first position.

13. The combination according to claim 9 wherein said locking means is a releasable locking means adapted for release to free said pedestal for rotation to said first position.

14. The combination according to claim 9 further including means for preventing rotation of said pedestal beyond said receptacle stabilizing position.

* * * * *